United States Patent
Shibata et al.

(10) Patent No.: US 10,695,747 B2
(45) Date of Patent: Jun. 30, 2020

(54) METHOD FOR PRODUCING POROUS CELLULOSE MEDIUM

(71) Applicant: DAICEL CORPORATION, Osaka-shi, Osaka (JP)

(72) Inventors: Toru Shibata, Himeji (JP); Yasuto Morishita, Himeji (JP); Keiji Nishihara, Myoko (JP)

(73) Assignee: DAICEL CORPORATION, Osaka-Shi (JP)

( * ) Notice: Subject to any disclaimer, the term of this patent is extended or adjusted under 35 U.S.C. 154(b) by 153 days.

(21) Appl. No.: 15/560,962

(22) PCT Filed: Apr. 1, 2016

(86) PCT No.: PCT/JP2016/060881
§ 371 (c)(1),
(2) Date: Sep. 22, 2017

(87) PCT Pub. No.: WO2016/159334
PCT Pub. Date: Oct. 6, 2016

(65) Prior Publication Data
US 2018/0043333 A1    Feb. 15, 2018

(30) Foreign Application Priority Data
Apr. 3, 2015 (JP) ................. 2015-077028

(51) Int. Cl.
*B01J 20/285* (2006.01)
*B01J 20/286* (2006.01)
(Continued)

(52) U.S. Cl.
CPC ........ *B01J 20/285* (2013.01); *B01D 15/3804* (2013.01); *B01D 15/3809* (2013.01);
(Continued)

(58) Field of Classification Search
CPC .... B01J 20/285; B01J 20/288; B01J 20/3071; B01J 20/3085; B01J 20/24; B01J 20/267;
(Continued)

(56) References Cited

U.S. PATENT DOCUMENTS

| 4,063,017 A | 12/1977 | Tsao et al. |
| 4,090,022 A | 5/1978 | Tsao et al. |

(Continued)

FOREIGN PATENT DOCUMENTS

| EP | 3 173 437 A1 | 5/2017 |
| JP | 52-129788 A | 10/1977 |

(Continued)

OTHER PUBLICATIONS

English translation WO 2015/046473 A1 (2015).*
(Continued)

*Primary Examiner* — John Kim
(74) *Attorney, Agent, or Firm* — Birch, Stewart, Kolasch & Birch, LLP (57) ABSTRACT

Provided are a technique for preparing a porous cellulose medium without using a special gelling agent for a solution in which cellulose acetate serving as a raw material is dissolved; and a porous cellulose medium and the like produced using the technique. A method for producing a porous cellulose medium comprises the step of preparing a flowable homogeneous composition comprising cellulose acetate, a basic compound, and a solvent including water, and gelling the composition by deacetylation reaction of the cellulose acetate.

11 Claims, 7 Drawing Sheets

(51) Int. Cl.
    *C07K 1/22* (2006.01)
    *C08J 9/28* (2006.01)
    *B01D 15/38* (2006.01)
    *C08B 15/00* (2006.01)
    *B01J 20/30* (2006.01)
    *B01J 20/24* (2006.01)
    *B01J 20/26* (2006.01)
    *B01J 20/288* (2006.01)

(52) U.S. Cl.
    CPC ............ *B01J 20/24* (2013.01); *B01J 20/267* (2013.01); *B01J 20/286* (2013.01); *B01J 20/288* (2013.01); *B01J 20/3071* (2013.01); *B01J 20/3085* (2013.01); *C07K 1/22* (2013.01); *C08B 15/00* (2013.01); *C08J 9/28* (2013.01); *B01J 2220/4831* (2013.01); *B01J 2220/82* (2013.01); *C08J 2205/022* (2013.01); *C08J 2301/02* (2013.01)

(58) Field of Classification Search
    CPC .................. B01J 20/286; B01J 2220/82; B01J 2220/4831; B01D 15/3809; B01D 15/3804; C07K 1/22; C08B 15/00; C08J 9/28; C08J 2205/022; C08J 2301/02
    See application file for complete search history.

(56) References Cited

U.S. PATENT DOCUMENTS

| | | |
|---|---|---|
| 4,118,449 A | 10/1978 | Rinde |
| 4,390,691 A | 6/1983 | Nishikawa et al. |
| 4,461,892 A | 7/1984 | Nishikawa et al. |
| 2013/0316892 A1 | 11/2013 | Nakamura et al. |

FOREIGN PATENT DOCUMENTS

| | | |
|---|---|---|
| JP | 57-038801 A | 3/1982 |
| JP | 57-159801 A | 10/1982 |
| JP | 62-277401 A | 12/1987 |
| JP | 63-095237 A | 4/1988 |
| JP | 2-208330 A | 8/1990 |
| JP | 6-254373 A | 9/1994 |
| WO | WO 2015/046473 A1 | 4/2015 |
| WO | WO 2016/013568 A1 | 1/2016 |

OTHER PUBLICATIONS

English translation WO 2016/013568 A1 (2016).*
English translation Japanese Patent Application No. 62277401 A (1987).*
Extended European Search Report dated Oct. 30, 2018, in European Patent Application No. 16773214.8.
Bai et al., "Preparation and characterization of crosslinked porous cellulose beads", Carbohydrate Polymers, vol. 64, 2006, pp. 402-407.
Chen et al., "Physical Characteristics of Porous Cellulose Beads as Supporting Material for Immobilized Enzymes", Biotechnology and Bioengineering, vol. XVIII, 1976, pp. 1507-1516.
International Search Report (PCT/ISA/210) issued in PCT/JP2016/060881, dated Jun. 7, 2016.
Reuvers et al., "Demixing and Gelation Behavior of Ternary Cellulose Acetate Solutions", Journal of Polymer Science: Part B: Polymer Physics, vol. 24, 1986, pp. 793-804.
Written Opinion (PCT/ISA/237) issued in PCT/JP2016/060881, dated Jun. 7, 2016.
Indian Office Action, dated Jan. 8, 2020, for Indian Application No. 20174703882, with an English translation.

\* cited by examiner

METHOD FOR PRODUCING POROUS CELLULOSE MEDIUM

TECHNICAL FIELD

The present invention relates to a method for producing a porous cellulose medium.

BACKGROUND ART

Polysaccharides represented by cellulose and derivatives thereof are used for a variety of applications. These microporous materials per se can serve as adsorbents, or when these microporous materials undergo a certain chemical modification on their surface, they can be provided with a function such as adsorption or separation.

One of such examples will now be described. Along with the prevalence of enzyme utilization or the development of biopharmaceuticals, the separation and purification of biopolymers such as proteins have become one of the important technical issues. Chromatography is an important means for solving this issue. Chromatography uses a separating agent in which a certain atomic group (often referred to as a selector) that interacts with an intended material or an impurity to be removed is bound to a solid referred to as a matrix.

An extremely important property of a material for separating a biopolymer is that it does not non-specifically adsorb proteins, and therefore, polysaccharides are valued for use as the matrix. Moreover, the presence of a large number of hydroxyl groups in the molecules of polysaccharides allows the selector to be readily bound via ether linkages or ester linkages using the hydroxyl groups as a scaffold, which is also an important factor that makes polysaccharides valued for use as the matrix.

For the separation and purification of a biopolymer, generally, a method is used in which the matrix is bound with a selector having a certain affinity for an intended molecule, and after the adsorption of the intended molecule, the adsorbed intended molecule is liberated and collected in a certain manner. In order to obtain a large amount of the intended molecule, the matrix is demanded to allow binding of a large amount of the selector, and have a porous structure that allows free entry and exit of the intended molecule, in order to allow the selector and the biopolymer having a high molecular weight to be efficiently interacted with each other. In other words, when the matrix is packed into a column to perform size exclusion chromatography, the matrix needs to exhibit an exclusion limit greater than the combined size of the molecule to be purified and the ligand.

This matrix is typically used by being packed as particles into a tube referred to as a column. In recent years, however, attention has been drawn to a new form referred to as a monolith, which is an integral porous material. This is used for the same application by being contained in a container such as a small tube referred to as a capillary, or a column. The monolith can also be used as a filtration membrane, if it has a relatively small thickness and a large area.

One factor for the ease of use of this matrix is its high physical strength, in addition to the selectivity for the target to be separated. Specifically, when a liquid or gas is passed during chromatography or filtration, a matrix having a low elastic modulus will undergo compressive deformation or breakage, and as a result, the flow of the liquid within the chromatographic column will become uneven, or even clogging will occur, leading to a significant deterioration in the separation efficiency of the column. In view of this, high physical strength is an important property, and in this respect, cellulose is an outstanding material among polysaccharides.

Additionally, cellulose has alcoholic hydroxyl groups on the surface as a general characteristic of polysaccharides, and thus, has advantages in that, for example, it is capable of binding a variety of atomic groups by chemical reactions, or is available in abundance and at relatively low cost in the form of a highly pure raw material.

For the foregoing reasons, porous cellulose particles for the main purpose of separating and purifying biopolymers have been developed. Among methods for producing such porous cellulose particles, many methods involve dissolving cellulose in a certain manner, followed by regeneration, while some methods use organic acid esters as starting materials. Direct dissolution of cellulose per se can be difficult in that a special solvent is required, or the viscosity of the solution is very high. On the other hand, the methods using organic acid esters as starting materials utilize the following advantages, for example: organic acid esters can be dissolved in many solvents; organic acid esters of cellulose are industrially supplied with stable quality, at various binding rates or degrees of polymerization with various organic acids; and the ester linkages can be readily broken down to regenerate cellulose.

Patent Literature 1, for example, describes a method for producing such cellulose particles, which includes dispersing, in an aqueous medium, a solution of a cellulose organic acid ester dissolved in an organic solvent such as a halogenated hydrocarbon to form microdroplets of the ester solution, and adding a hydrolysis accelerator such as an ammonium salt thereto to cause hydrolysis of the ester, thus forming cellulose microparticles.

Patent Literature 2 describes a method for producing porous spherical particles, which includes dissolving, in an organic solvent, a cellulose fatty acid ester and a gelling agent for the cellulose fatty acid ester to form a solution, adding the solution into an aqueous medium under stirring to form droplets, further adding a coagulation accelerator to convert the cellulose fatty acid ester contained in the droplets into gel particles, and removing the gelling agent, coagulation accelerator, and solvent from the resulting particles.

Patent Literature 3 describes a method for preparing a particulate cellulose gel, which includes dissolving cellulose in a mixed solution of paraformaldehyde and dimethylsulfoxide, dispersing the solution in a dispersion medium, and then introducing a silicon compound serving as a coagulating agent into the dispersion to cause gelation and coagulation of droplets of the cellulose dispersion.

Non Patent Literature 1 describes that porous particles are formed by dissolving cellulose acetate in a water-soluble organic solvent (a mixed solvent of acetone and DMSO), and dispersing the solution in water, which causes the solution containing cellulose acetate to coagulate upon contact with water.

Non Patent Literature 2 describes that cellulose particles (beads) are obtained by dissolving cellulose diacetate in DMSO, subsequently adding anhydrous sodium sulfate and stirring the mixture, and introducing the mixture into an acid coagulating bath (hydrochloric acid). Moreover, a means for increasing the porosity of the beads by immersing extracted beads in a large amount of warm water to remove sodium sulfate is described.

CITATION LIST

Patent Literature

Patent Literature 1: Japanese Patent Laid-Open No. 62-277401
Patent Literature 2: Japanese Patent Laid-Open No. 63-95237
Patent Literature 3: Japanese Patent Laid-Open No. 57-159801
Non Patent Literature 1: Chen, L. F.; Tsao, G T. Biotechnol. Bioeng. 1976, 18, 1507
Non Patent Literature 2: Bai, Y.-X.; Li, Y.-F. Carbohydr. Polym. 2006, 64, 402
Non Patent Literature 3: A. J. Reuvers et al., J. Polym. Sci., 1986, 24, 793

SUMMARY OF INVENTION

Technical Problem

According to the techniques described in Patent Literatures 1 and 2, a solvent containing a halogenated hydrocarbon is used in both methods, and during the preparation of the particles, the solvent is removed by vaporization, which requires a large amount of energy and an apparatus for collecting the vaporized solvent. Moreover, according to the method using a coagulation accelerator or a coagulating agent as described in Patent Literature 2 or 3, a dense layer of the cellulose fatty acid ester may form in the portion of contact with the coagulation accelerator or the like in the formed droplets, possibly resulting in a distorted particle shape. Thus, when the gelation is performed after the formation of droplets as described in Patent Literature 2 or 3, the reaction may become nonuniform.

Moreover, Non Patent Literature 1 describes cross-linking the beads by subjecting the formed beads to a cross-linking reaction using formaldehyde and hydrochloric acid. Non Patent Literature 2 describes using a pore forming agent for providing the particles with pores. In both Non Patent Literatures 1 and 2, the formation of particles includes the step of treating the surface, and the removal of the substances used for the surface treatment is required to obtain the porous cellulose particles.

A main object of the present invention is to provide a technique for preparing a porous cellulose medium without using a special gelling agent for a solution in which cellulose acetate serving as a raw material is dissolved. Specifically, the present invention aims to provide a technique for preparing a porous cellulose medium, whereby a porous cellulose medium applicable to a separating agent can be obtained by subjecting a homogeneous composition containing cellulose acetate serving as a raw material, a basic substance, and a solvent including water to deacetylation reaction of the cellulose acetate, thereby gelling the composition without causing migration of the substances out of the system.

Solution to Problem

The present invention was made in view of the foregoing circumstances. It has been reported in a paper that a homogeneous composition containing a solvent including water and cellulose acetate undergoes a phase transition (liquid-gel) at a certain temperature or lower to form a gel (Non Patent Literature 3).

Apart from this, the present inventors found that a cellulose medium that maintains its porous structure and has excellent characteristics can be achieved by obtaining a gel having a shape suitable for the purpose, such as a mass shape or a particulate shape, by subjecting a homogeneous composition containing cellulose acetate, a basic substance, and a solvent including water to deacetylation of the cellulose acetate, without the addition of a non-solvent (gelling agent).

A summary of the present invention is as set forth below.

[1] A method for producing a porous cellulose medium comprising the step of preparing a flowable homogeneous composition comprising cellulose acetate, a basic compound, and a solvent including water, and gelling the composition by deacetylation reaction of the cellulose acetate.

[2] A method for producing spherical porous cellulose particles comprising the step of obtaining a dispersion by dispersing a flowable homogeneous composition comprising cellulose acetate, a basic compound, and a solvent including water in a dispersion medium not miscible with the homogeneous composition, and forming gelled particles composed of the composition by gelling the composition by deacetylation reaction of the cellulose acetate contained in the obtained dispersion.

[3] The method for producing spherical porous cellulose particles according to [2], which comprises, after the preceding step, the step of adding a separating solvent for separating the obtained gelled particles to the dispersion in which the gelled particles are formed, thereby separating the gelled particles into the separating solvent.

[4] The method for producing spherical porous cellulose particles according to [3], wherein the separating solvent is water, methanol, ethanol, 2-propanol, acetamide, formamide, or a mixture of at least two of these solvents.

[5] A method for producing a porous cellulose monolith comprising the step of placing a flowable homogeneous composition comprising cellulose acetate, a basic compound, and a solvent including water in a mold container, and gelling the homogeneous composition within the mold container by deacetylation reaction of the cellulose acetate.

[6] The method according to any of [1] to [5], wherein the solvent including water in the homogeneous composition includes an organic solvent that is miscible with water, but is not miscible with a saturated hydrocarbon.

[7] The method according to [6], wherein the organic solvent is an aprotic polar solvent.

[8] A method for producing an adsorbent comprising the step of immobilizing an affinity ligand onto the porous cellulose medium obtained using the method according to [1], the spherical porous cellulose particles obtained using the method according to any of [2] to [4], or the porous cellulose monolith obtained using the method according to [5].

[9] The method for producing an adsorbent according to [8], wherein the affinity ligand is one or more selected from the group consisting of protein A, protein G, protein L, and a functional variant thereof.

[10]

A method for purifying a target substance comprising:
a first step of contacting the adsorbent according to [8] or [9] with a mixture comprising the target substance to allow the target substance to bind to the affinity ligand immobilized onto the adsorbent; and
a second step of separating the target substance bound to the affinity ligand on the adsorbent.

Advantageous Effects of Invention

According to the present invention, in the production of a porous cellulose medium such as porous cellulose particles, there is no need to use an organic chlorine-based solvent such as a halogenated hydrocarbon for dissolving cellulose acetate; moreover, in the gelation of the composition containing cellulose acetate, gelation of the homogeneous composition caused by deacetylation reaction is utilized, which allows the pore size of the obtained cellulose medium to be uniform.

DESCRIPTION OF EMBODIMENTS

The method for producing a porous cellulose medium according to the present invention utilizes the property of a homogeneous composition containing cellulose acetate, a basic substance, and a solvent including water to undergo a phase transition from liquid to gel by deacetylation reaction, and involves forming a gel composed of the homogeneous composition, and using, as a porous medium, the gel in which the cellulose acetate has been converted into cellulose by deacetylation.

In the present invention, the phase transition from liquid to gel by deacetylation is a phenomenon in which a liquid composition having flowability loses its flowability as the deacetylation reaction proceeds. For example, the phenomenon in which a decrease in temperature results in an increase in viscosity is observed in many homogeneous solution compositions, and when such a composition in liquid form turns into a gel, it completely loses its flowability, and often becomes cloudy. In the present invention, gelation is induced by deacetylation reaction, without the addition of a reagent or the like other than a basic substance.

<Cellulose Acetate>

Cellulose acetate used in the present invention is not limited as long as the composition containing a basic substance, a solvent including water, and the cellulose acetate undergoes the phase transition by deacetylation. Physical properties of cellulose acetate may be represented by the degree of polymerization and the degree of substitution, for example.

The degree of polymerization is preferably 50 or more as the weight average, in order to increase the mechanical strength of the resulting porous cellulose particles, and prevent the elution thereof into the solvent or the like during use. On the other hand, with regard to the upper limit of the degree of polymerization, any commercially available cellulose acetate can be used.

The degree of substitution has a strong effect on the solubility of cellulose acetate. The degree of substitution refers to a numerical value indicating the number of substituted hydroxyl groups out of the three hydroxyl groups per glucose residue in the cellulose. In the case of an acetate, the degree of substitution may be expressed in terms of acetic acid content or acetyl group content, and these values can be converted between each other. Generally, cellulose acetate having a degree of substitution around 2.8 to 2.9 is distributed as triacetate, and cellulose acetate having a degree of substitution around 2.5 is distributed as diacetate. In the present invention, cellulose acetate having any degree of substitution may be used as long as it provides a composition that undergoes the phase transition.

Cellulose acetate that is commonly distributed is available in the following forms: so-called cellulose diacetate used for general purposes such as textile materials (in particular, a typical product has a degree of substitution of acetyl groups of 2.5, and is represented by an acetic acid content (degree of acetylation) around 55%); and cellulose triacetate used as film materials for pictures or liquid crystal displays (having a degree of substitution of acetyl groups of 2.8 to 2.9, and represented by an acetic acid content (degree of acetylation) around 60%). Cellulose acetate having a degree of substitution around 1 (although such cellulose acetate should be referred to as monoacetate, since it is not commonly distributed, the name "monoacetate" has not been established as a common name) may even dissolve in water, and has a wide range of options for polar solvent systems. Such cellulose acetate of a grade that is not commonly distributed can be obtained, for example, by adding a calculated amount of a base into a solution of cellulose acetate having a higher degree of substitution to perform solvolysis, or by hydrolyzing a hydrous acetic acid solution of the cellulose acetate using an acid catalyst such as sulfuric acid, and stopping the reaction at an appropriate time (neutralizing the sulfuric acid). For example, the above-described cellulose acetate can be obtained by reacting diacetate (cellulose diacetate) as a starting material with 1.5 equivalents of a base per glucose unit. As the base, hydrazine or hydroxylamine is easy to use because they are neutral molecules and thus, are readily miscible with many organic solvents, and are fast to react. That is, any base that is miscible with the raw material solution can be used, for example, a hydroxide such as a quaternary ammonium hydroxide.

While the boundary between triacetate, diacetate, and monoacetate in terms of the degree of acetylation is not clearly defined, in the present invention, triacetate is defined as having a degree of acetylation of 2.7 or more, diacetate is defined as having a degree of acetylation of 1.5 or more and less than 2.7, and monoacetate is defined as having a degree of acetylation of 0.5 or more and less than 1.5, for convenience sake.

<Composition in the Present Invention>

The composition used in the method of the present invention is a homogeneous composition containing the above-described cellulose acetate, a basic substance, an organic solvent, and water. The homogeneous composition refers to a composition in which the basic substance, the solvent including water, and the cellulose acetate are homogeneously mixed.

In the present invention, the phase transition from liquid to gel by deacetylation is a phenomenon in which a liquid composition having flowability before deacetylation loses its flowability after deacetylation. In the present invention, the conditions under which deacetylation occurs to cause the phase transition from liquid to gel can be adjusted by appropriately changing the composition of this composition, or the degree of polymerization or the degree of substitution of the cellulose acetate to be incorporated.

The content of each of the cellulose acetate, basic substance, and solvent including water in the composition is not limited as long as it causes deacetylation of the cellulose acetate.

The content of the cellulose acetate in the composition is preferably 1 to 20 wt %, and more preferably 4 to 15 wt %, in order to provide the resulting porous cellulose with a pore size suitable for practical use and an appropriate hardness.

Examples of the basic compound to be incorporated into the composition include ammonia, hydrazine, and alkyl-substituted products thereof; guanidines, amidines, and substituted products thereof; diamines; hydroxyalkylamines such as hydroxylamine and ethanolamine; amines such as alkylamines, for example, ethylamine and propylamine; metal hydroxides such as sodium hydroxide, potassium hydroxide, and lithium hydroxide; and inorganic bases such as hydroxylated quaternary ammonium, metal alcoholates, and hydroxamic acid salts.

In an exemplary embodiment, the amount of the basic substance in the composition may be 0.5 to 10 moles, and is preferably 1 to 5 moles, per mole of acetyl groups of the cellulose acetate. The inclusion of the basic substance at this ratio allows deacetylation to occur satisfactorily.

In the method for producing a porous cellulose medium according to the present invention, a flowable homogeneous composition containing cellulose acetate, a basic substance, and a solvent including water is prepared, and the composition is gelled by deacetylation reaction of the cellulose acetate. That is, the homogeneous composition is gelled as the deacetylation of the cellulose acetate in the homogeneous composition proceeds.

In a conventional method such as that in Patent Literature 1, deacetylation is performed after gelation; however, in the present invention, deacetylation and gelation occur simultaneously. To prepare the homogeneous composition, the components may be mixed together at once; however, the dissolution of a cellulose derivative is typically lengthy, and it is undesirable if the deacetylation reaction partially proceeds before the cellulose derivative is completely dissolved. Thus, the homogeneous composition is preferably prepared by preparing in advance a solution in which the cellulose acetate is dissolved in the solvent including water, separately preparing a solution in which the basic compound is dissolved in the solvent including water, and homogeneously mixing these solutions. Note that when cellulose monoacetate is used as the cellulose acetate, water can be used alone (without including an organic solvent) as the solvent.

Upon completion of the preparation of the homogeneous composition, the deacetylation reaction starts. The rate of deacetylation reaction can be adjusted by adjusting the temperature of the homogeneous composition, or adjusting the type or concentration of the basic compound.

In an exemplary embodiment, the solvent including water to be incorporated into the composition may be an organic solvent in addition to water. The ratio of water to the organic solvent may be any ratio that initially causes dissolution of the cellulose acetate, and causes gelation of the composition by the reaction. For example, in an exemplary embodiment, the weight ratio of water to the organic solvent may be 5:95 to 90:10.

As reported in Non Patent Literature 3 listed above, an acetone/water mixture system for CDA, as well as a dioxane/water mixture system may be used as the solvent including water. However, the organic solvents contained in these systems are difficult to handle in that, because considerable amounts of these organic solvents dissolve into liquid paraffins, or the vapor pressures of these organic solvents are high, they tend to cause unexpected gelation due to the migration of substances caused by factors other than the temperature during the dispersion process. Thus, a solvent is desirable that has low solubility in nonpolar liquids such as liquid paraffins, and is unlikely to undergo a change in concentration due to evaporation. Preferred as solvents having such attributes are those that are not homogeneously miscible with a saturated hydrocarbon such as hexane.

Organic solvents having high dissolving power for cellulose acetate in general and having the above-described properties include many aprotic polar solvents, for example, one or more selected from halogen-free solvents such as DMSO, sulfolane, dimethylsulfone, N-methylpyrrolidone, N,N-dimethylacetamide, N,N'-dimethylformamide, N,N'-dimethylimidazolidinone, hexamethylphosphoric triamide, and tetramethylurea. Among the above, one or more solvents selected from DMSO, N-methylpyrrolidone, and N,N-dimethylacetamide are preferably used in an exemplary embodiment.

The temperature at which the deacetylation reaction occurs is preferably −10 to 100° C., and more preferably 0 to 70° C., in view of handleability in the production of the porous cellulose medium. Note that when an inorganic base is used as the basic substance, the reaction temperature may be −10 to 50° C. in an exemplary embodiment, in order to prevent the reaction from proceeding unnecessarily rapidly.

The reaction conditions cannot be uniquely determined because the above-described compounds have different solubilities and reaction rates for the solvent. A known method can be used, and the acetyl groups may be removed to a level suitable for the purpose of use.

The time required for deacetylation, i.e., the time required for the gelation of the homogeneous composition, is 1 minute to 48 hours, and preferably about 5 minutes to 24 hours, for example. When the homogeneous composition is dispersed in a dispersion medium to obtain the particles, the time required for deacetylation is preferably shorter in view of the dispersion stability.

After the completion of the reaction, the resulting product is washed with a solvent that does not adversely affect the porous cellulose, and a preservative is optionally added.

<Shape of the Porous Cellulose Medium>

The porous cellulose medium produced by the method of the present invention can be used either as spherical particles or a monolith. To prepare the spherical particles or monolith, a different process for controlling the shape is adopted before the above-described specific composition is subjected to deacetylation of the cellulose acetate for gelation.

For the production of the monolith, the above-described homogeneous composition is caused to undergo the phase transition in a container having a desired shape. On the other hand, for the production of the particles, generally, the homogeneous composition as a solution is caused to undergo a change in temperature while being dispersed in a dispersion medium not miscible with the homogeneous composition, to undergo the phase transition. Specific methods for producing the monolith and for producing the spherical particles will be briefly described hereinafter.

<Spherical Particles>

An exemplary embodiment of the method for producing spherical porous cellulose particles of the present invention includes the step of obtaining a dispersion by dispersing a flowable homogeneous composition containing cellulose acetate, a basic compound, and a solvent including water in a dispersion medium not miscible with the homogeneous composition, and forming gelled particles composed of the composition by gelling the composition by deacetylation reaction of the cellulose acetate contained in the obtained dispersion.

The method may further include, after the preceding step, the step of adding a separating solvent for separating the obtained gelled particles to the dispersion in which the gelled particles are formed, thereby separating the gelled particles into the separating solvent.

In the method for producing spherical porous cellulose particles of the present invention, a dispersion medium for dispersing the composition is used. Any dispersion medium may be used in the present invention as long as it is not miscible with water and the organic solvent contained in the composition to cause unintentional gelation or an extreme change in the phase transition temperature of the composition, which may adversely affect the pore size of the intended spherical porous cellulose particles.

In order to prevent aggregation of the composition during dispersion of the composition, the dispersion medium preferably has a certain degree of viscosity during the dispersion of the composition. The viscosity of the dispersion medium may be 0.2 to 20 Pa·S at 25° C., for example.

The dispersion medium is preferably a nonpolar dispersion medium so that it is not miscible with water and the organic solvent contained in the composition. Examples of such nonpolar dispersion media include hydrocarbons having 20 or more carbon atoms such as liquid paraffins and petrolatum, silicone oils, and fluorinated hydrocarbons.

Petrolatum rapidly loses its flowability once the temperature is reduced below a specific softening temperature. Therefore, when the particles of the dispersed liquid for forming a gel tend to aggregate into a mass, the dispersion may be prepared first at the softening temperature or higher, and then the dispersion may be cooled below the softening temperature, so as to prevent migration and contact of droplets for forming a gel. Petrolatum is thus effective for the purpose of increasing the yield of the particles. The softening temperature of petrolatum differs depending on the type, and may be selected as appropriate.

The above-described basic compounds may be used as the basic compound to be incorporated into the composition. The amount of the basic compound may be in the range of amounts as defined above relative to acetyl groups of the cellulose acetate. Likewise, the amounts of the other components in the homogeneous composition may be in the range of amounts as defined above in <Composition in the Present Invention>.

After being dispersed in the dispersion medium, the composition containing the cellulose acetate of the present invention needs to maintain its dispersed state until it is gelled by deacetylation. For this purpose, it is preferred to add an appropriate dispersion stabilizer to the dispersion medium.

The dispersion stabilizer may be any dispersion stabilizer effective at increasing the stability of the dispersed state of the composition, and reducing the rate of aggregation of the particles composed of the composition. Examples of such dispersion stabilizers include esters of polyhydric alcohols such as glycerol, sorbitan, polyglycerol, and sucrose with higher carboxylic acids, and modified silicones containing small amounts of polar groups. Other commercially available dispersion stabilizers can also be used.

Various methods are already available for dispersing the composition containing the cellulose acetate into the dispersion medium, including a method that provides a wide range of particle size distributions and a method that provides a monodispersed particle size. One example of a method suitable for preparing a product with a uniform particle size is a method using an apparatus generally called a microreactor, in which the liquid dispersion medium is passed at an appropriate rate, while the homogeneous composition for forming a gel is injected through a finer nozzle.

Alternatively, the following various methods may be used, for example: a method in which the flowable homogeneous composition of the present invention is extruded into the dispersion medium through membranes of a fixed pore size; a method in which the flowable homogeneous composition of the present invention is placed in an inner cylinder provided with pores of a fixed size, and the inner cylinder is rotated in the dispersion medium, which causes the homogeneous composition for forming a gel to be extruded by centrifugal force; a method in which the dispersion medium optionally containing a dispersion stabilizer and the flowable homogeneous composition are fed into a column packed with beads of a fixed size; a method in which the flowable homogeneous composition is injected into the dispersion medium through a vibration nozzle; and a method utilizing (ultra)sonic waves.

In the Examples, the simplest method that utilizes stirring and yet provides mixtures of various particle sizes will be described by way of example. This method involves adding the homogeneous composition to the dispersion medium, and then producing substantially spherical particles composed of the composition, and simultaneously gelling the homogeneous composition in the form of dispersion droplets by deacetylation. The conditions for stirring and mixing may be selected as appropriate, depending on the intended average particle size.

In an exemplary embodiment, the composition dispersed in the dispersion medium may be allowed to stand for 1 to 48 hours, preferably about 10 to 30 hours, so that the deacetylation reaction proceeds in the particles composed of the homogeneous composition.

Note that in an exemplary embodiment, the temperature of the dispersion medium when the composition containing the cellulose acetate is added to the dispersion medium may be a temperature at which the composition is maintained in liquid state. Specifically, in an exemplary embodiment, the temperature of the dispersion medium may be set to about 50 to 80° C. Setting the temperature of the dispersion medium at such a temperature facilitates stirring and mixing of the composition. It is preferred to add and disperse the homogeneous composition into the dispersion medium, while the homogeneous composition is retaining its flowability.

<Separating Solvent>

While the subsequent process is not limited to a particular process, in the Examples of the present invention, a separating solvent for extracting the gelled cellulose particles from the dispersion medium may be used. In an exemplary embodiment, for example, a separating solvent may be added to the dispersion medium in which the composition is dispersed, in order to separate, from the dispersion medium, only the cellulose particles as gelled particles in the particles composed of the gelled composition.

The separating solvent to be used is a separating solvent that is not miscible with the dispersion medium, and is miscible with water and the organic solvent that may be contained in the composition, although it does not dissolve the cellulose contained in the gelled composition. This prevents re-dissolution of the cellulose in the gelled composition.

Examples of such separating solvents include water, methanol, ethanol, 2-propanol, acetamide, formamide, and a mixture thereof. Among the above, water may be used because of its handleability in an exemplary embodiment.

While it is possible to directly filter off the gelled particles of the cellulose dispersed in the dispersion medium, this increases the risk of deformation or breakage of the gelled particles, because the dispersion medium, which generally has a high viscosity, is subjected to pressure during filtration. The pressure during filtration may be reduced by adding to the dispersion medium a low-viscosity liquid miscible with the dispersion medium.

The obtained porous cellulose particles are washed in an appropriate manner such as with water or ethanol, and are typically stored in a water-wet state. When drying the porous cellulose particles, an appropriate amount of a saccharide, glycerol, or the like is added. For long-term storage in a water-wet state, a preservative such as an alcohol or sodium azide is added to prevent corruption. Alternatively, the porous cellulose particles to which glycerol, a saccharide, urea, or the like has been added may be dried. For use, the porous cellulose particles are packed into a column in accordance with a conventional method.

Among the porous cellulose particles obtained using the method of the present invention, particles having a substantially spherical to spherical shape with a particle size (maximum size) of 30 to 300 μm may be screened in accordance with known appropriate classification, and used as a chromatographic packing material. An example of chromatography may be size exclusion chromatography.

The fact that the porous cellulose particles can be used for size exclusion chromatography means that when the porous cellulose particles are bound to an appropriate ligand, they can also be used for chromatographic separation using various modes other than the size exclusion. Examples of such modes include ion exchange, hydrophobic, and affinity modes.

In general, for the separation and purification of polymers produced by biotechnology, such as hormones, enzymes, and antibody drugs, it is preferred to use a matrix having a pore size that allows sufficient entry of these substances. Specifically, when gel filtration chromatography is performed using a column packed with the porous cellulose particles, and using water as the mobile phase, fractionation is expected to occur in a certain region of molecular weights ranging from approximately $10^3$ to $10^7$ as converted into the molecular weights of polyethylene glycols.

The elution of standard materials (polyethylene glycols) having molecular weights of $10^4$ to $10^6$ at different times by GPC in Example 1 shows that the pore size of the matrix that can be prepared using the method of the present invention is suitable for separation and purification of these materials. The pore size can be finely adjusted by changing the cellulose acetate concentration in the composition to be gelled which contains the solvent including water and the cellulose acetate, or depending on the gelling conditions (for example, by adjusting the rate of cooling of the homogeneous composition).

A method for preparing an adsorbent for use in the affinity mode will be described hereinafter. A protein may be used as the affinity ligand. Examples of proteins that can be used in the present invention include substances having molecular weights of 3 to 300 kDa. and preferably 30 to 150 kDa, and having an affinity for the protein to be separated such as an antibody. Among the above, protein A, protein G, protein L, and a functional variant thereof are preferred as the affinity ligand because of their high selectivity when used for separating an antibody protein.

For the principal purpose of separating an antibody, the ligand is preferably a ligand that can specifically bind to a portion of an immunoglobulin. The above-described functional variant refers to a protein having at least one modification in a natural amino acid sequence, and still retaining at least one function accompanying the natural sequence. A natural sequence originally contains a naturally occurring amino acid sequence. Examples of alterations to the amino acids include the substitution of one or more amino acids with other amino acids, the deletion of one or more amino acids and/or the addition of one or more amino acids, and any combination thereof. In an exemplary embodiment, a combination of the addition, deletion, and substitution of amino acids may be made in the natural sequence. The functional variant may contain a fragment or domain of the protein. The amino acid sequence of the functional variant may be at least 70% identical, at least 75% identical, at least 80% identical, at least 85% identical, at least 90% identical, at least 95% identical, and at least 98% identical to the natural amino acid sequence, and still retains at least one function accompanying the natural sequence.

The amount of the protein supported on the porous cellulose particles is preferably 1.0 to 25 parts by weight based on 100 parts by weight of the porous cellulose particles. Further, in an exemplary embodiment, the volume of the protein supported on the porous cellulose particles may be 1 to 50 mg per ml of the porous cellulose particles.

By further including the step of immobilizing the above-described affinity ligand into the method for producing the porous cellulose medium produced using the method of the present invention, an adsorbent to which the affinity ligand is bound can be produced. This adsorbent can also be used as a separating agent for affinity chromatography.

An exemplary embodiment of the method for producing an adsorbent may be described as follows. First, the method for producing an adsorbent may include the step of subjecting the porous cellulose particles produced using the above-described method to a cross-linking reaction using a cross-linking agent. The cross-linking method is not limited to a particular method, and a cross-linking agent, for example, a halohydrin such as epichlorohydrin, epibromohydrin, or dichlorohydrin, bisoxirane, or polyoxirane, can be used.

Next, the method for producing an adsorbent may include the step of activating the cross-linked cellulose particles. For example, a known reactive functional group may be introduced to activate the cross-linked cellulose particles. When the cross-linked cellulose particles are activated using, for example, cyanogen bromide (CNBr), N,N'-disuccinimidyl carbonate (DSC), an epoxide, and an activated carboxylic acid (NHS ester), an original functional group of the porous cellulose particles can be replaced with a functional group more reactive with the compound to be immobilized as the ligand. Then, an adsorbent is produced by way of the subsequent step of immobilizing the ligand onto the porous cellulose particles by reacting the porous cellulose particles with the compound to be immobilized as the ligand.

As an alternative to the above-described method, a method for producing an adsorbent may be used in which condensation or cross-linking is performed by adding a condensation reagent such as carbodiimide or a reagent having a plurality of functional groups in the molecule such as glutaraldehyde, into the system containing the porous cellulose particles and the compound to be immobilized as the ligand, to thereby immobilize the ligand onto the porous cellulose particles.

In another exemplary embodiment of binding the porous cellulose particles to the affinity ligand, a formyl group may be introduced into the cellulose and the cellulose particles, and the formyl group may be reacted with an amino group of a protein. The reaction of introducing a formyl group may be performed, for example, by oxidizing a polysaccharide having vicinal hydroxyl groups using a periodate oxidation method, and producing a formyl group on the sugar chain.

An alternative method may be used in which a formyl group is introduced through any of various spacers obtained by, for example, reacting a glyceryl group obtained by the ring opening of an epoxy group with a periodate. For example, an amino sugar such as glucosamine can be used as a spacer.

Then, the formyl group of the porous cellulose particles can be bound to a protein such as protein A, using a known method. In an exemplary embodiment, for example, the porous cellulose particles into which a formyl group has been introduced via an amino sugar such as glucosamine as the spacer may be reacted with a solution containing protein A. An example of such a method is described in Japanese Patent Laid-Open No. 2008-279366.

<Monolith>

A monolith is an integral mass of a porous raw material. In chromatography using the above-described particulate packing material, although an eluent passes through even the micropores of the particles, it passes more through gaps between particles. In contrast, the monolith allows an eluent to pass through the micropores of the integral porous material. Therefore, typically, in the monolith, the solids content is lower than that in the particulate packing material to reduce resistance to the flow of the eluent. The monolith, however, is completely identical to the packing material in terms of essential mechanism of separation, except for the case where it is used as a filtration material.

The method for producing a porous cellulose monolith of the present invention includes the step of placing a flowable homogeneous composition containing cellulose acetate, a basic compound, and a solvent including water in a mold container, and gelling the homogeneous composition within the mold container by deacetylation reaction of the cellulose acetate. The same cellulose acetate, basic compound, and solvent including water as those used for the preparation of the spherical particles can be used in this method. Likewise, the same amount of each of the components contained in the homogeneous composition as that used for the preparation of the spherical particles can be used.

In liquid chromatography, it is extremely important that an eluent pass at the same velocity in every portion of the separating agent, and a so-called piston flow be created. In the packing material, variations in the properties of individual particles are equalized by mixing, and thus, a certain degree of difference in the properties between particles is acceptable. It is, however, important for the packing material to have uniform gaps between particles, which plays a significant part in the liquid flow. To achieve this, the technique used in packing the packing material into a container called a column is a key factor.

In the monolith, on the other hand, it is extremely important that the resulting porous structure be homogeneous in a direction perpendicular to the flow of the eluent, and no gaps through which the liquid readily passes be formed between the monolith and the container. The porous material homogeneous in the perpendicular direction as referred to herein cannot be prepared through contact with a gelling agent (precipitant), or through evaporation of the solvent, which is a known technique.

The method of the present invention utilizing gelation by deacetylation reaction of the cellulose acetate is suitable for preparing the monolith, in that it can provide a homogeneous gel if the equalization of the temperature of the raw material composition is faster than the gelation rate.

The monolith is prepared as follows. The above-described homogeneous composition containing a basic compound, a solvent including water, and cellulose acetate is introduced into a mold container having a desired shape. Then, a gel composed of the composition is formed by causing deacetylation reaction of the cellulose acetate by allowing the composition to stand at a temperature of about 0 to 100° C. for 10 minutes to 48 hours, preferably about 1 to 24 hours. This gel can be directly used as a separating agent. Alternatively, this gel can be washed with an appropriate solvent after being removed from the container, and then used as a separating agent. Drying is generally avoided because it may cause deformation of the shape of the monolith, or cause a loss of the microporous structure; however, drying can be performed in the presence of an appropriate nonvolatile additive.

Substances suitable as such nonvolatile additives include saccharides and sugar alcohols such as glycerol, sucrose, trehalose, and starch syrup; various amides; and polar compounds such as DMSO.

In order to evaluate the prepared monolith, the monolith needs to be contained in an appropriate container such that no gaps are formed, or no local compaction is present, as described above. Any known method may be used to achieve this. In general, when the monolith is produced by gelation, it undergoes a certain shrinkage, often resulting in gaps being formed between the container and the monolith. In this case, the monolith can be contained in the container without gaps being present therebetween, for example by preventing the formation of gaps by modifying the wall surface of the container into a chemical structure having a strong affinity for cellulosic substances (for example, by bonding cellulose to the surface), or by utilizing shrinkage or swelling of the gel due to an environmental change, or by making the size of the container adaptable (adjustable).

As with the above-described spherical particles, the prepared monolith can be bound to the affinity ligand and used as a separating agent or adsorbent for affinity chromatography. The affinity ligand that can be bound to the monolith is the same as that used for the spherical particles, and the affinity ligand can be bound using the same method as that used for the spherical particles.

<Purification Method Using the Porous Cellulose Medium of the Present Invention in Affinity Mode>

A method for producing various target molecules can be provided through the use of the above-described adsorbent obtained by binding the affinity ligand to the porous cellulose medium prepared by the method of the present invention.

Examples of target molecules include proteins such as immunoglobulins. Examples of immunoglobulins include polyclonal antibodies, monoclonal antibodies, and functional fragments thereof.

The purification method of the present invention includes the following steps: a first step of contacting an adsorbent obtained by binding an affinity ligand to the porous cellulose medium prepared by the method of the present invention with a mixture containing a target substance to allow the target substance to bind to the affinity ligand; and a second step of separating the target substance bound to the affinity ligand on the adsorbent.

The target substance bound to the affinity ligand on the adsorbent may be separated by, for example, changing the pH between the first and second steps, or changing the salt concentration. Specifically, the pH in the first step may be set to a neutral pH of 6 to 8, for example, and the pH in the second step may be set to an acidic pH of less than 6, for example. The salt concentration may be set to less than 0.1 M in the first step and then set to 0.1 M or more in the second step, or may be set to 0.1 M or more in the first step and then set to less than 0.1 M in the second step.

EXAMPLES

The present invention will be described hereinafter in more detail with reference to examples; however, the scope of the present invention is in no way limited to these examples only.

Experimental Example

Confirmation of Gelation by Deacetylation Reaction 15.5 g of VTR cellulose diacetate (degree of acetylation: 54.75%, viscosity of a 6% acetone solution: 0.117 Pa·s (25° C.)) was dissolved in 174.4 g of DMSO. While 30.0 g of the DMSO solution of cellulose diacetate was kept at 60° C., a mixed solution of 2.0 g of hydrazine monohydrate, 2.1 g of water, and 6.4 g of DMSO was added thereto, and the mixture was stirred well. A portion of this mixture was heated to 40° C. for 12 hours. After this, gelation of the mixture was confirmed.

Example 1: Preparation of Porous Cellulose Particles

Figure 1:
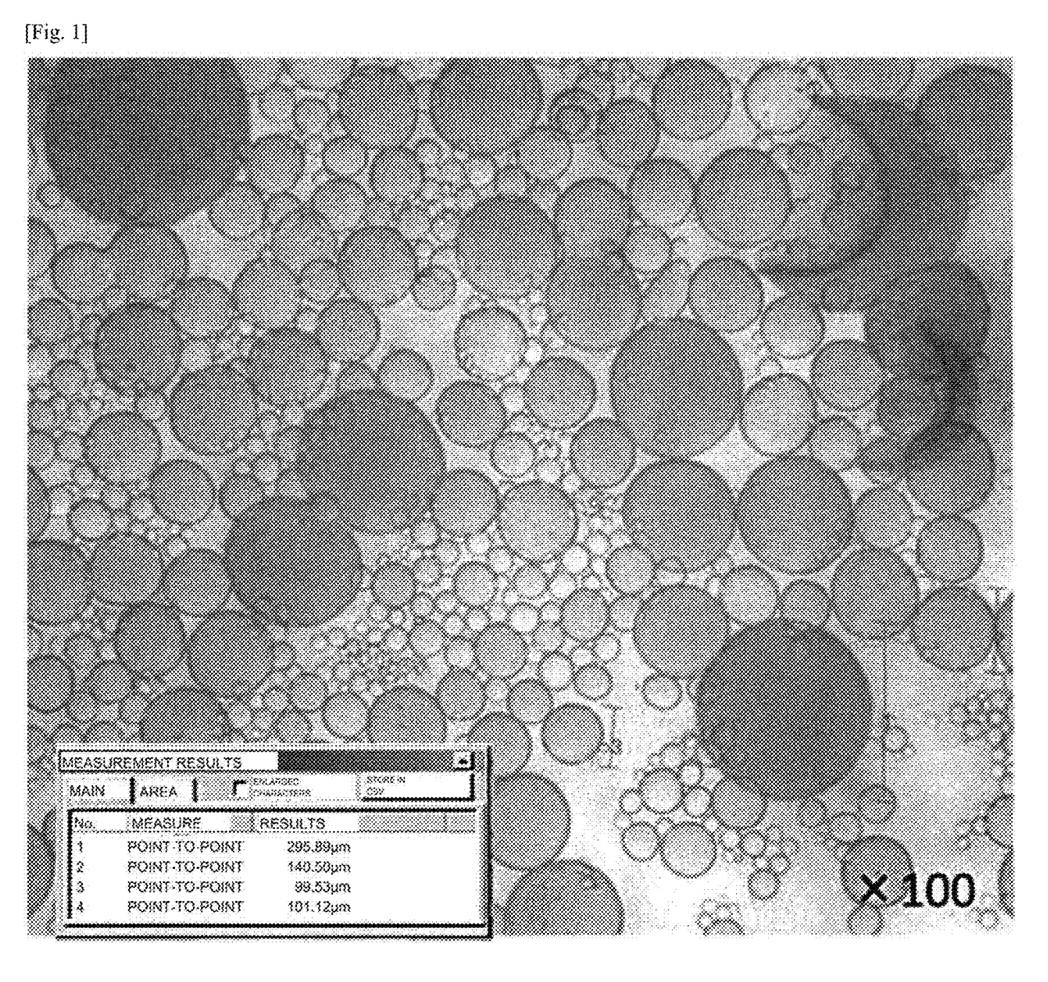
FIG. 1 is an optical micrograph of porous cellulose particles obtained using the method of the present invention (Example 1).

A separable flask was charged with 360 g of White Vaseline (from Wako Pure Chemical Industries, Ltd., Wako first grade) and 0.63 g of emulsifier TSG10 (from Nihon Emulsion Co., Ltd.), and kept at 70° C. in an oil bath to melt these components. While 30.0 g of the DMSO solution of cellulose acetate prepared as above was kept at 60° C. a mixed solution of 2.0 g of hydrazine monohydrate, 2.1 g of water, and 6.4 g of DMSO was added thereto, and the mixture was stirred well. This cellulose diacetate solution was added to the separable flask, and the mixture was stirred at about 600 rpm for 5 minutes, using a disperser with a diameter of 4 cm. The resulting dispersion was solidified by cooling to 40° C. in an ice bath, and gelled by deacetylation by being allowed to stand at 40° C. for 24 hours. To the dispersion was added 300 mL of water, the mixture was heated to 70° C., and after the dissolution of the dispersion, the particles were extracted and separated by slowly stirring. After the separation of the aqueous phase, 300 mL of water was added again, and the extraction and separation was performed by slowly stirring. The extracted aqueous phase was filtered through a glass filter, and the particles were repeatedly washed with ethanol and water. FIG. 1 shows a photograph of the obtained particles taken with a microscope, which reveals a substantially spherical shape of the particles.

Example 2: Preparation of Porous Cellulose Particles

Figure 2:
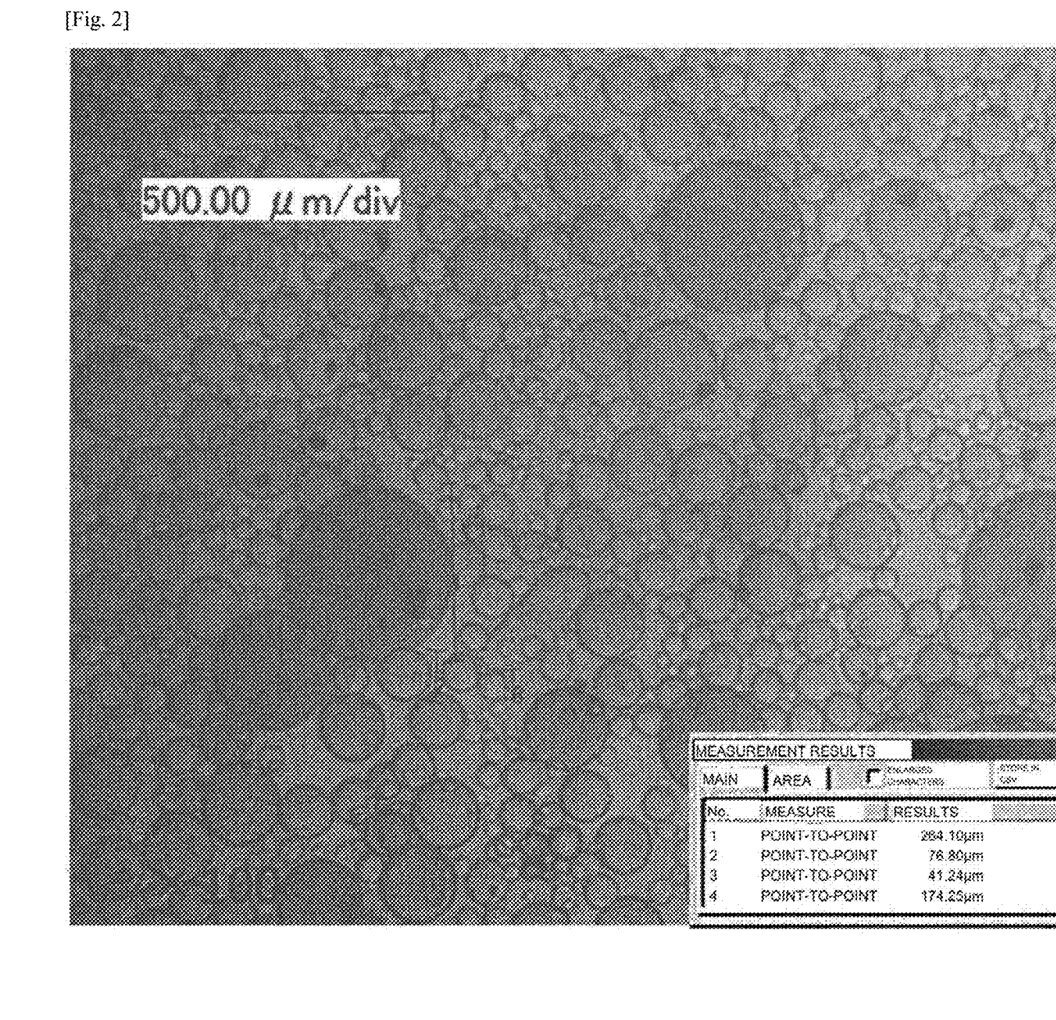
FIG. 2 is an optical micrograph of porous cellulose particles obtained using the method of the present invention (Example 2).
Figure 3:
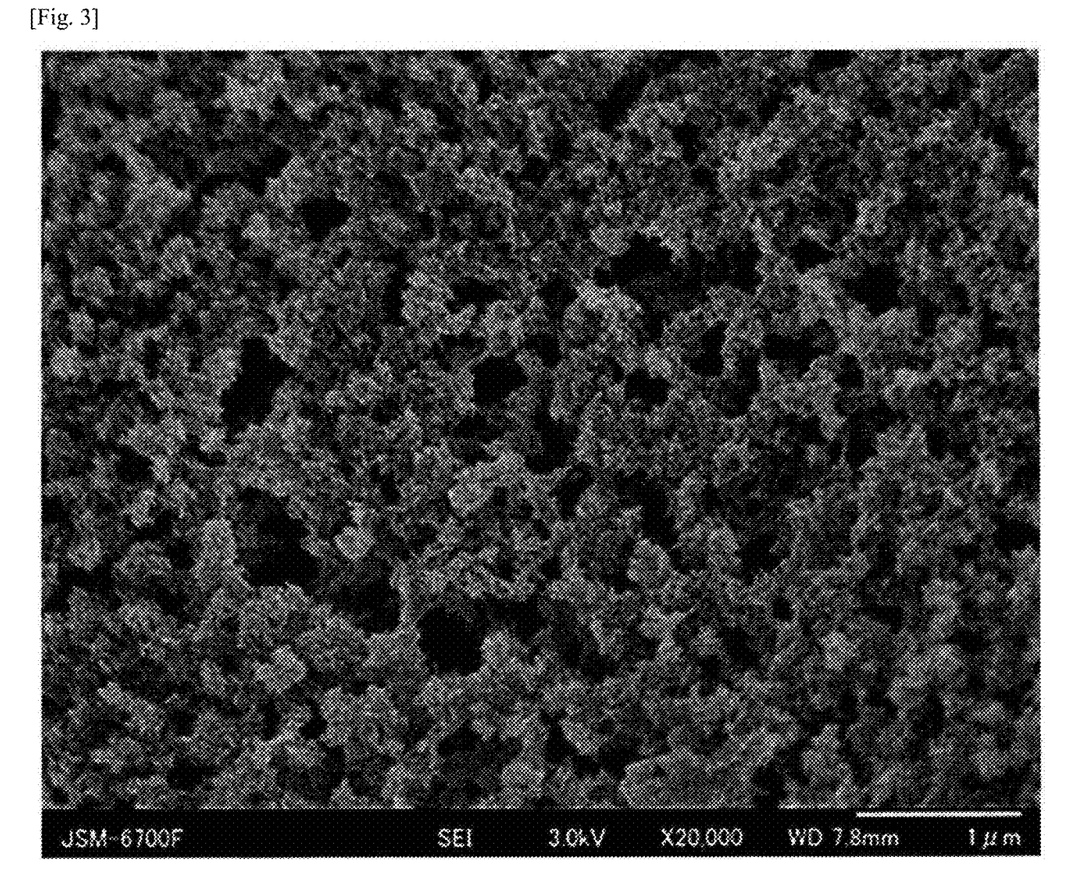
FIG. 3 is an electron micrograph of porous cellulose particles obtained using the method of the present invention (Example 2).

A separable flask was charged with 733 g of White Vaseline (from Wako Pure Chemical Industries. Ltd., Wako first grade) and 1.1 g of emulsifier TSG10 (from Nihon Emulsion Co., Ltd.), and kept at 70° C. in an oil bath to melt these components. While 60.1 g of the DMSO solution of cellulose diacetate prepared as in Example 1 was kept at 60° C., a mixed solution of 3.8 g of hydrazine monohydrate, 8.8 g of water, and 26.9 g of DMSO was added thereto, and the mixture was stirred well. This mixed solution was added to the separable flask, and a disperser with a diameter of 80 mm was inserted into the mixed solution and the mixed solution was stirred at about 400 rpm for 5 minutes. The resulting dispersion was solidified by cooling to 40° C. in an ice bath, and gelled by deacetylation by being allowed to stand at 40° C. for 24 hours. To the dispersion was added 300 mL of water, the mixture was heated to 70° C., and after the dissolution of the dispersion, the particles were extracted and separated by slowly stirring. After the separation of the aqueous phase, 200 mL of water was added again, and the extraction and separation was performed by slowly stirring. The extracted aqueous phase was filtered through a glass filter, and the particles were repeatedly washed with ethanol and water. FIG. 2 shows a micrograph of the obtained particles. A portion of the obtained particles was replaced with 30% ethanol, 50% ethanol, 70% ethanol, 90% ethanol, or ethanol, and further replaced with a 5/5, 7/3, 9/1, or 10/0 mixed solution of t-butyl alcohol/ethanol, and then the resulting particles were subjected to freeze-drying treatment. Observation of an electron micrograph of the freeze-dried particles showed that the particles had a porous surface (FIG. 3).

Example 3: Preparation of Porous Cellulose Particles 15.3 g of VTR cellulose diacetate (degree of acetylation: 54.75%, viscosity of a 6% acetone solution: 0.117 Pa·s (25° C.)) was dissolved in 172.4 g of DMSO.

Figure 4:
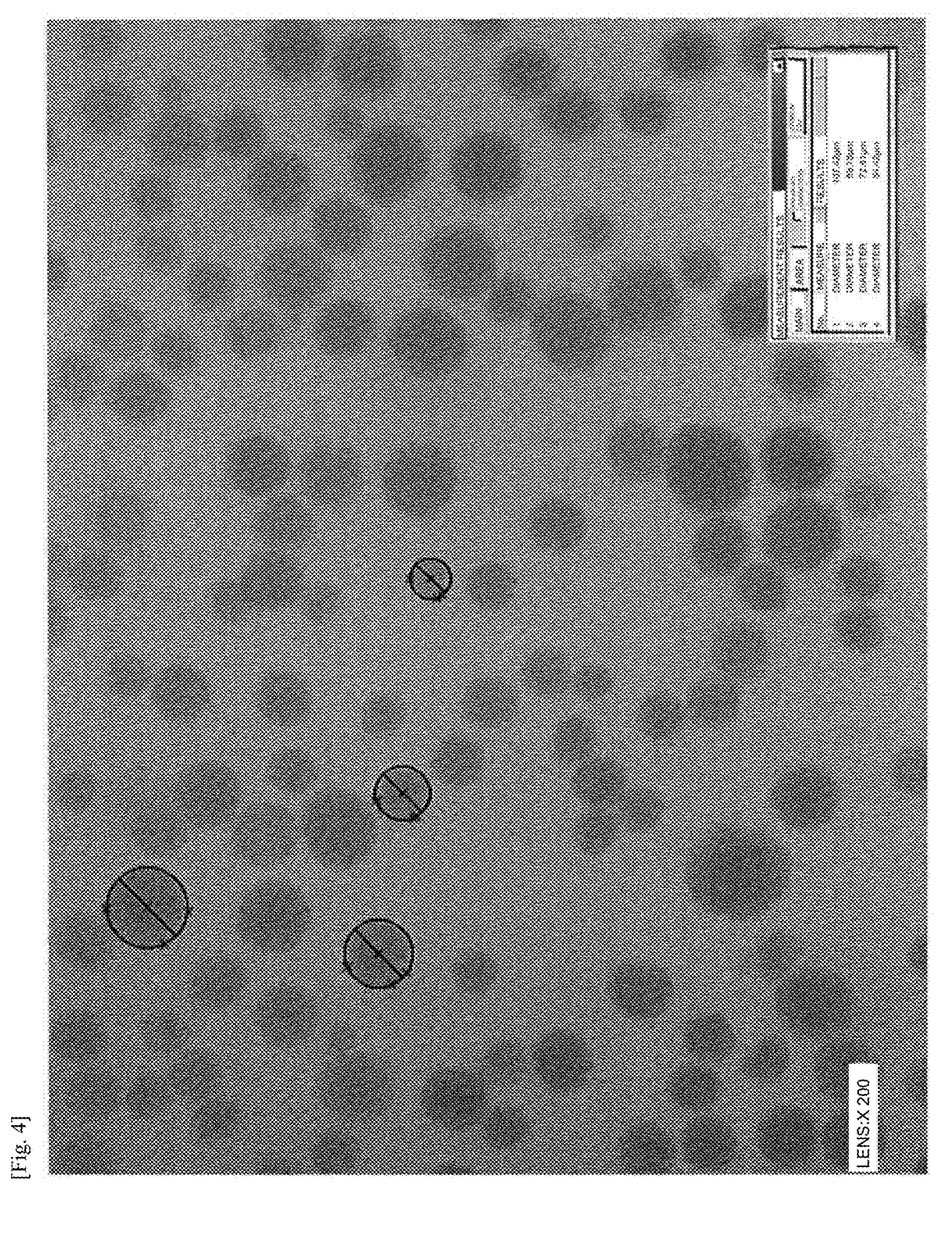
FIG. 4 is an optical micrograph of porous cellulose particles obtained using the method of the present invention (Example 3).
Figure 5:
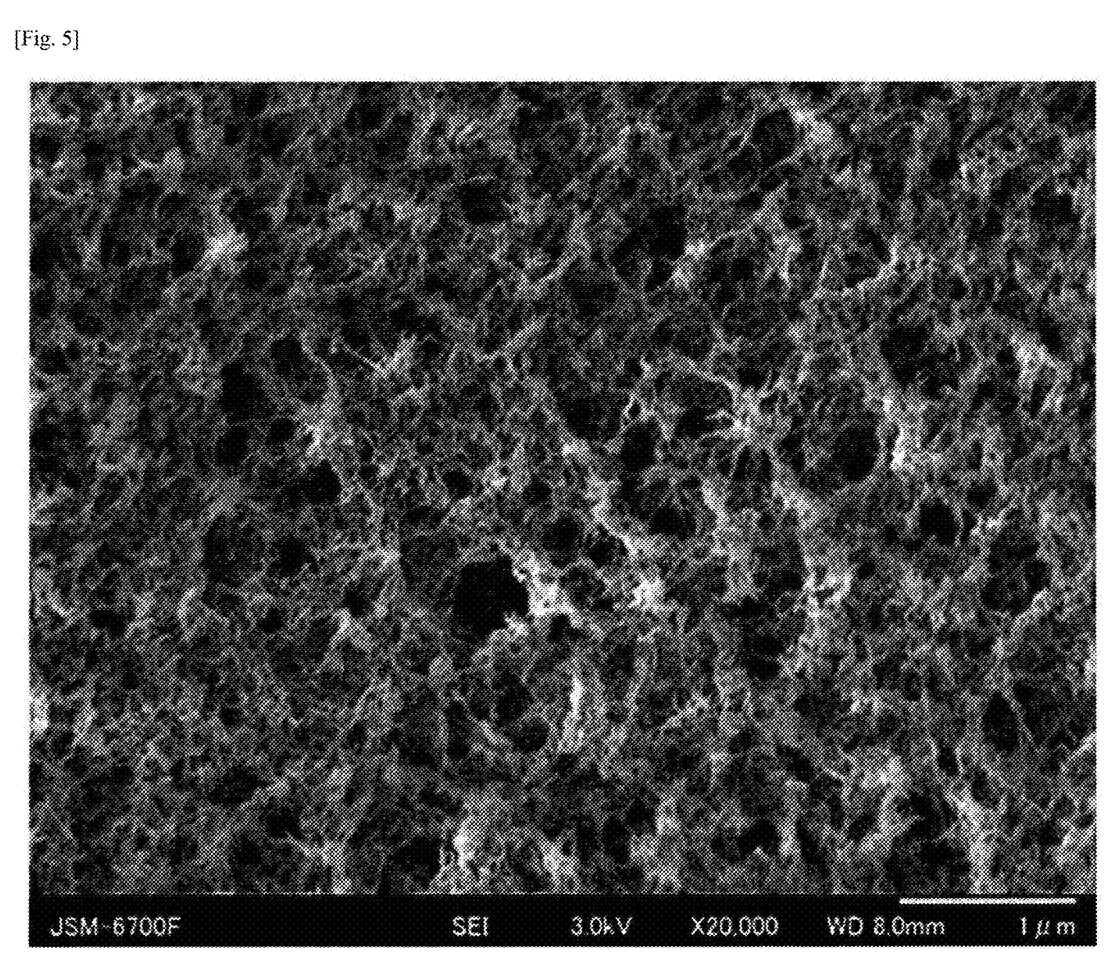
FIG. 5 is an electron micrograph of porous cellulose particles obtained using the method of the present invention (Example 3).

A separable flask was charged with 733 g of White Vaseline (from Wako Pure Chemical Industries, Ltd., Wako first grade) and 1.4 g of emulsifier TSG10 (from Nihon Emulsion Co., Ltd.), and kept at 70° C. in an oil bath to melt these components. While 60.6 g of the DMSO solution of cellulose diacetate prepared as above was kept at 60° C., a mixed solution of 9.1 g of hydrazine monohydrate, 13.3 g of water, and 40.7 g of DMSO was added thereto, and the mixture was stirred well. This mixed solution was added to the separable flask, and a disperser with a diameter of 80 mm was inserted into the mixed solution and the mixed solution was stirred at about 325 rpm for 5 minutes. The resulting dispersion was solidified by cooling to 40° C. in an ice bath, and gelled by deacetylation by being allowed to stand at 40° C. for 24 hours. To the dispersion was added 300 mL of water, the mixture was heated to 70° C., and after the dissolution of the dispersion, the particles were extracted and separated by slowly stirring. After the separation of the aqueous phase, 200 mL of water was added again, and the extraction and separation was performed by slowly stirring. The extracted aqueous phase was filtered through a glass filter, and the particles were repeatedly washed with ethanol and water. The obtained cellulose particles dispersed in water were sized using a 150-μm, 106-μm, or 53-μm stainless screen. FIG. 4 shows a micrograph of a 53- to 106-μm portion of the particles stained with Congo red. FIG. 5 shows an electron micrograph of the particles after freeze-drying. As shown in the electron micrograph, porous cellulose particles were observed.

Example 4: Preparation of Cellulose Particles Using Cellulose Monoacetate (1) Synthesis of Cellulose Monoacetate To 1 part by weight of cellulose acetate (from Daicel Corporation; trade name "L-50"; total degree of substitution of acetyl groups: 2.43; 6% viscosity: 110 mPa·s), 5.1 parts by weight of acetic acid and 2.0 parts by weight of water were added, and the mixture was stirred for 3 hours to dissolve the cellulose acetate. To this solution was added 0.13 part by weight of sulfuric acid, and the resulting solution was kept at 70° C. to cause hydrolysis. After 1 hour, 0.67 part by weight of water was added over 5 minutes; then, after 2 hours, 1.33 parts by weight of water was added over 10 minutes, and the reaction was further continued for 6 hours. After this, the reaction mixture was cooled to 25° C., a precipitate was produced by adding 15 parts by weight of a mixed solution containing an equal volume of acetone and methanol, and this precipitate was deliquored by centrifugation with a filter cloth. To the resulting solvent-containing cake having a solids content of about 15 wt %, water was added in an amount equivalent to 14 parts by weight relative to the raw material cellulose acetate, and the mixture was stirred to dissolve the precipitate. An amount of methanol equivalent to 4 times the weight of the resulting solution was added to the solution, which produced a precipitate again, and the precipitate was deliquored and collected. The following procedure was repeated twice: water was added again and the precipitate was dissolved, methanol was added and a precipitate was produced, and the precipitate was deliquored and collected. The resulting solvent-containing precipitate was dispersed in 8 parts by weight of methanol containing 0.004% potassium carbonate, and the precipitate was deliquored and collected. This procedure was repeated twice. Then, the resulting precipitate was vacuum dried at 50° C. to obtain cellulose monoacetate for use as a raw material.

(2) Preparation of Porous Cellulose Particles

In 11.3 g of water, 2.0 g of the cellulose monoacetate obtained above was dissolved.

Figure 6:
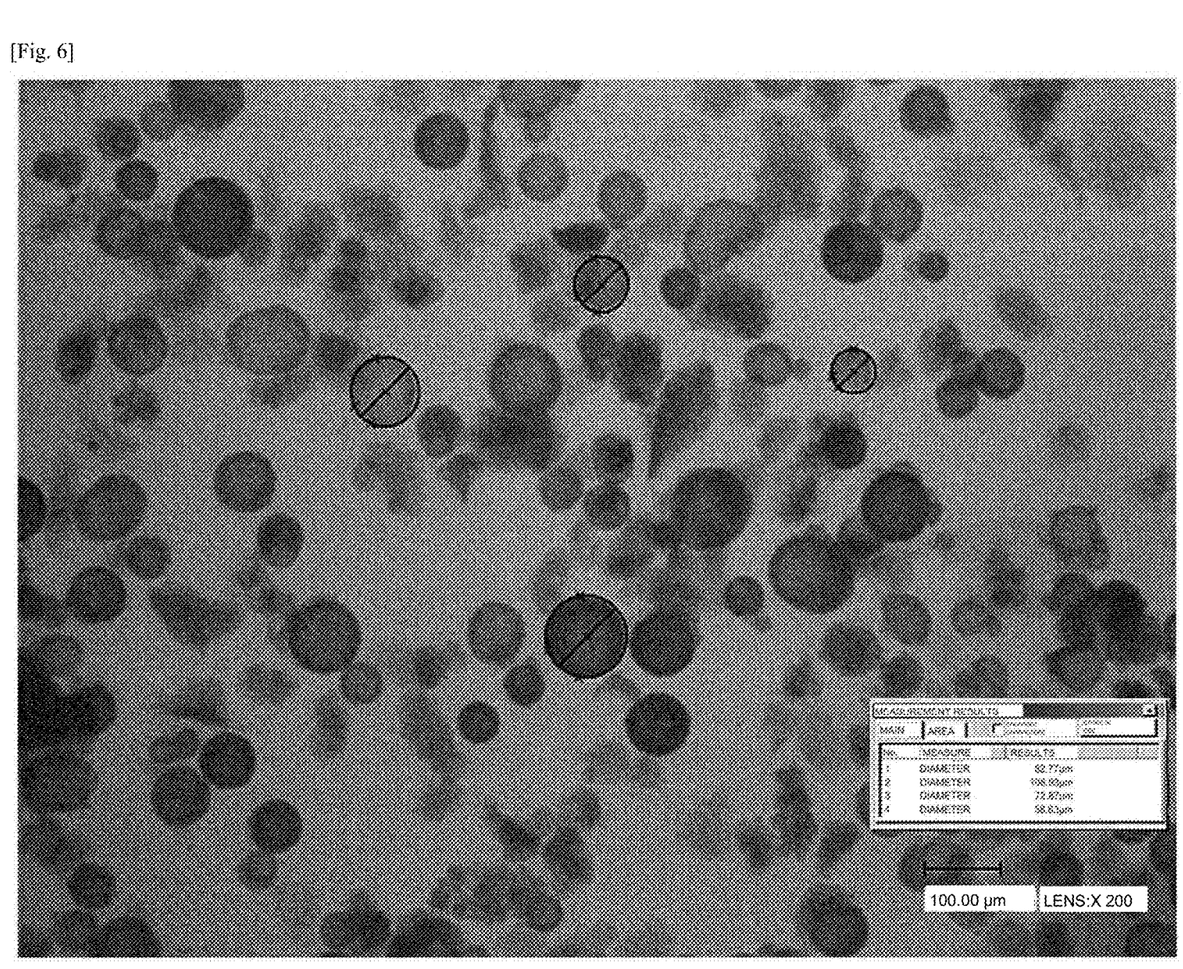
FIG. 6 is an optical micrograph of porous cellulose particles obtained using the method of the present invention (Example 4).

A separable flask was charged with 132 g of a liquid paraffin (from Kanto Chemical Co., Inc.; Cica first grade) and 0.67 g of emulsifier SPAN80 (from Tokyo Chemical Industry Co., Ltd.), and the contents were mixed while cooling in an ice bath. 11.7 g of the above-described aqueous solution of cellulose monoacetate cooled to 5 to 10° C. in an ice bath and 6.7 g of a 4 wt % aqueous solution of sodium hydroxide were mixed well, this mixed solution was rapidly added to the separable flask, and a disperser with a diameter of 40 mm was inserted into the mixed solution and the mixed solution was stirred at about 350 rpm for 2 minutes. The resulting dispersion was gelled by deacetylation by being allowed to stand for 10 minutes. To the dispersion was added 100 mL of water, the mixture was heated to 25° C., and the particles were extracted and separated by slowly stirring for 3 hours. After the separation of the aqueous phase, 100 mL of water was added again, and the extraction and separation was performed by slowly stirring. A small amount of potassium hydroxide was added to the extracted aqueous phase, and the aqueous phase was slowly stirred and then allowed to stand overnight. The aqueous phase was neutralized by the addition of acetic acid, and passed through a 25-μm screen. Then, the aqueous phase was filtered through a glass filter, and the particles were repeatedly washed with ethanol and water. The obtained cellulose particles dispersed in water were sized using a 150-μm, 106-μm, or 53-μm stainless screen. FIG. 6 shows a micrograph of a 53- to 106-μm portion of the particles stained with Congo red.

Example 5

Size Exclusion Chromatography

Figure 7:
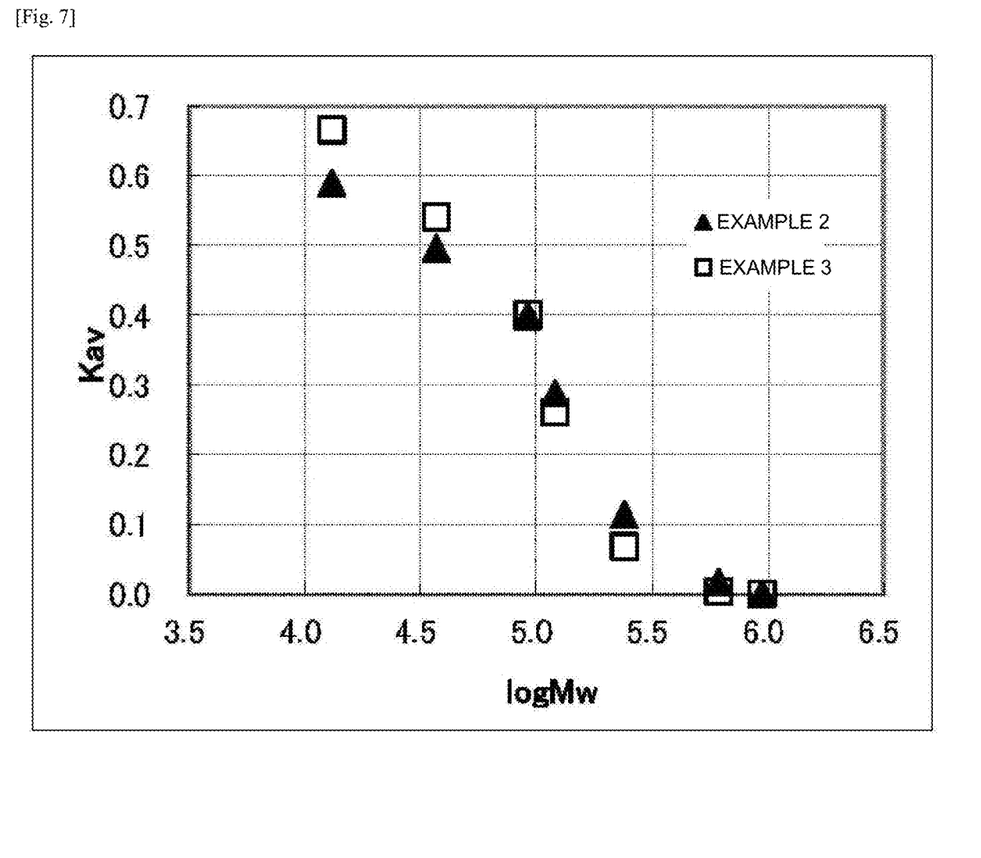
FIG. 7 is a diagram showing a calibration curve prepared by separating standard polyethylene oxide using the porous cellulose particles obtained in Example 2 or 3.

The cellulose particles prepared in Examples 2 and 3 dispersed in water were sized using a 150-, 106-, or 53-μm stainless screen. About 7 mL of a 53- to 106-μm portion of the particles was packed into columns with an inner diameter of 10 mm and a height of 100 mm, the samples of standard polyethylene oxide shown in Table 1 were injected into the columns, using pure water as the mobile phase, under the conditions summarized below, and the samples were detected with a differential refractometer detector. A calibration curve drawn in accordance with a conventional method is shown in FIG. 7.

Columns used: HR 10/100 (GE Healthcare)
Tricorn 10/100 (GE Healthcare)
Flow rate: 0.10 ml/min
Eluent: ultrapure water (degassed)
Standard materials: TSKgel standard polyethylene oxide (purchased from Tosoh Corporation)
Each sample was diluted to 2 mg/mL with ultrapure water.

TABLE 1

| Sample | Da |
|---|---|
| SE-150 | 940000 |
| SE-70 | 610000 |
| SE-30 | 240000 |
| SE-15 | 120000 |
| SE-8 | 92000 |
| SE-5 | 37000 |
| SE-2 | 13000 |

The distribution coefficient (Kav) of each standard material was calculated based on the following equation:

$$Kav=(Ve-V0)/(Vt-V0)$$

wherein Ve is the retention volume (mL) of the sample, Vt is the column void volume (mL), and $V_0$ is the retention volume (mL) of SE-150.

Example 6

(1) Preparation of Cross-Linked Porous Cellulose Particles

To a 100 mL three-necked flask, a solution obtained by dissolving 10 mL of the porous cellulose particles obtained in Example 3 and 10.6 g of sodium sulfate in 28.8 g of water was added, and stirred at 50° C. 0.37 g of a 45 wt % aqueous solution of sodium hydroxide and 60 mg of sodium borohydride were added, and the mixture was stirred. 5.42 g of a 45 wt % aqueous solution of sodium hydroxide and 5.55 g of epichlorohydrin were each added in 10 equally divided amounts at intervals of 30 minutes over approximately 5 hours. After the completion of the addition, the reaction was performed at 50° C. for 19 hours. After cooling the reaction mixture to 40° C. or lower, 0.62 g of acetic acid was added for neutralization. The reaction mixture was filtered to collect the particles, and the particles were filtered and washed with pure water to obtain the intended cross-linked porous cellulose particles.

(2) Immobilization of Protein a onto the Cross-Linked Porous Cellulose Particles and Preparation of a Column The cross-linked porous cellulose particles obtained in (1) were filtered off through a glass filter, and the particles were washed with acetonitrile to obtain 3.3 mL of a support. The support was transferred into a flask, 10 mL of an acetonitrile solution containing 2.5 mL of acetonitrile and 55 mg of di(N-succinimidyl) carbonate [N,N'-Disuccinimidyl carbonate] was added, and the mixture was shaken at 4° C. and 180 rpm. Next, 1 mL of an acetonitrile solution containing 40 mg of N,N-dimethylaminopyridine was added, and the mixture was reacted with shaking for 18 hours. The reaction mixture was filtered off through a glass filter, and the particles were washed with 30 mL of acetonitrile, 30 mL of dioxane containing 5% acetic acid, 30 mL of methanol, and 30 mL of 2-propanol in this order to obtain an activated support. 1 mL of the activated support was taken into a glass filter and washed with a coupling buffer (0.1 M sodium phosphate, pH 7.0). The activated support was transferred into a flask, and 168 μL of a protein A-containing solution containing 53.6 mg/mL of protein A (rSPA, Repligen) and 2 mL of the coupling buffer were added and immobilized by shaking at 5° C. and 130 rpm for 22 hours. The resulting product was filtered off through a glass filter and washed with the coupling buffer. Measurement of the filtrate after the reaction using the Bradford method showed the immobilization of 9.0 mg of protein A per mL of the support. Next, the support was transferred into a flask, and 2 mL of 1M tris-hydrochloride (pH 8) was added to mask unreacted active groups by shaking at 25° C. and 130 rpm for 2 hours. The support was filtered off through a glass filter and washed alternately with a washing solution 1 (0.1 M tris-hydrochloride, 0.5 M sodium chloride, pH 8.0) and a washing solution 2 (0.1 M ammonium acetate buffer, 0.5 M sodium chloride, pH 4.0) for 3 cycles. 1 mL of the immobilized support was washed with pure water and packed into a Tricorn 5/50 column. Additionally, a column was prepared following the same procedure, using Sepharose 4 Fast Flow (GE Healthcare) (the amount of immobilized protein A: 10 mg/mL-gel).

(3) Antibody Adsorption Capacity of the Protein A-Immobilized Column

Each of the protein A-immobilized columns prepared in (2) was placed on the liquid chromatography apparatus AKTAexplore (GE Healthcare Bioscience) and equilibrated by passing an adsorption buffer (20 mM phosphate buffer, 150 mM sodium chloride, pH 7.2) at 1 mL/min or 0.4 mL/min, and then human serum-derived γ-globulin (Wako Pure Chemical Industries, Ltd.) adjusted to 1 mg/mL was injected. The injection was continued until 15% of the absorbance at 280 nm of the eluate was reached, and after washing with the adsorption buffer, the adsorption buffer was replaced with 20 mM citric acid (pH 2.4), and adsorbed components were eluted.

The dynamic adsorption capacity (DBC) was calculated based on the amount of the sample injected until the absorbance at 280 nm of the eluate excluding non-adsorbed components reached 10% of the absorbance of the injected sample. Table 2 shows the DBC for each of the immobilized columns.

TABLE 2

| Flow Rate | Protein A-Immobilized Cross-linked Porous Cellulose Particles | Protein A-Immobilized Sepharose 4 Fast Flow |
|---|---|---|
| 1.0 mL/min. | 13 mg | 8 mg |
| 0.4 mL/min. | 23 mg | 22 mg |

INDUSTRIAL APPLICABILITY

According to the method of the present invention, a porous cellulose acetate medium is produced by utilizing the property of a specific composition containing cellulose acetate to form a gel by deacetylation reaction.

This allows the pore size to be uniform during the gelation process of the cellulose acetate. This differs from conventional methods for producing porous cellulose media in which the solvent is evaporated during the process of pore formation, which causes migration of substances. Further, according to the method of the present invention, the pore size of the obtained porous cellulose medium is as large as approximately several thousands of angstroms. The hardness of the porous cellulose medium obtained using the method of the present invention is approximately equal to that of conventionally available commercial products. The porous medium obtained using the method of the present invention, either in the form of spherical particles or a monolith, is useful as an adsorbent or separating agent. In particular, the adsorbent bound to an affinity ligand can be used for the separation of various target substances.

The invention claimed is:

1. A method for producing spherical porous cellulose particles comprising the step of obtaining a dispersion by dispersing a flowable homogeneous composition comprising cellulose acetate, a basic compound, and a solvent including water in a dispersion medium not miscible with the homogeneous composition, and forming gelled particles composed of the composition by gelling the composition by deacetylation reaction of the cellulose acetate contained in the obtained dispersion.

2. The method for producing spherical porous cellulose particles according to claim 1, which comprises, after the preceding step, the step of adding a separating solvent for separating the obtained gelled particles to the dispersion in which the gelled particles are formed, thereby separating the gelled particles into the separating solvent.

3. The method according to claim 2, wherein the separating solvent is water, methanol, ethanol, 2-propanol, acetamide, formamide, or a mixture of at least two of these solvents.

4. The method according to claim 1, wherein the solvent including water in the homogeneous composition includes an organic solvent that is miscible with water, but is not miscible with a saturated hydrocarbon.

5. The method according to claim 4, wherein the organic solvent is an aprotic polar solvent.

6. A method for producing a porous cellulose monolith comprising the step of placing a flowable homogeneous composition comprising cellulose acetate, a basic compound, and a solvent including water in a mold container, and gelling the homogeneous composition within the mold container by deacetylation reaction of the cellulose acetate.

7. The method according to claim 6, wherein the solvent including water in the homogeneous composition includes an organic solvent that is miscible with water, but is not miscible with a saturated hydrocarbon.

8. A method for producing an adsorbent, comprising:
obtaining a dispersion by dispersing a flowable homogeneous composition comprising cellulose acetate, a basic compound, and a solvent including water in a dispersion medium not miscible with the homogeneous composition,
forming gelled particles composed of the composition by gelling the composition by deacetylation reaction of the cellulose acetate contained in the obtained dispersion to produce spherical porous cellulose particles, and immobilizing an affinity ligand onto the spherical porous cellulose particles.

9. The method for producing an adsorbent according to claim 8, wherein the affinity ligand is one or more selected from the group consisting of protein A, protein G, protein L, and a functional variant thereof.

10. A method for purifying a target substance comprising:

obtaining a dispersion by dispersing a flowable homogeneous composition comprising cellulose acetate, a basic compound, and a solvent including water in a dispersion medium not miscible with the homogeneous composition;

forming gelled particles composed of the composition by gelling the composition by deacetylation reaction of the cellulose acetate contained in the obtained dispersion to produce spherical porous cellulose particles;

immobilizing an affinity ligand onto the spherical porous cellulose particles to produce an adsorbent;

contacting the adsorbent with a mixture comprising the target substance to allow the target substance to bind to the affinity ligand immobilized onto the adsorbent; and separating the target substance bound to the affinity ligand on the adsorbent.

11. A method for producing an adsorbent, comprising:

placing a flowable homogeneous composition comprising cellulose acetate, a basic compound, and a solvent including water in a mold container, gelling the homogeneous composition within the mold container by deacetylation reaction of the cellulose acetate to produce a porous cellulose monolith, and immobilizing an affinity ligand onto the porous cellulose monolith.

* * * * *